(12) United States Patent
Fanselow et al.

(10) Patent No.: US 7,122,709 B2
(45) Date of Patent: Oct. 17, 2006

(54) METHOD FOR OBTAINING ETHANOL (75) Inventors: Dan L. Fanselow, White Bear Lake, MN (US); James S. Mrozinski, Oakdale, MN (US); Todd W. Johnson, Minneapolis, MN (US); Brinda B. Lakshmi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 753 days.

(21) Appl. No.: 10/387,697

(22) Filed: Mar. 13, 2003

(65) Prior Publication Data

US 2004/0181101 A1 Sep. 16, 2004

(51) Int. Cl.
*C07C 29/86* (2006.01)
*C07C 29/76* (2006.01)
*C07C 27/74* (2006.01)

(52) U.S. Cl. ...................... 568/918; 568/913
(58) Field of Classification Search .............. 568/913, 568/918
See application file for complete search history.

(56) References Cited

U.S. PATENT DOCUMENTS

| | | |
|---|---|---|
| 3,332,746 A | 7/1967 | Claff et al. |
| 3,428,553 A | 2/1969 | Shiah |
| 3,796,313 A | 3/1974 | Bigt et al. |
| 3,801,404 A | 4/1974 | Druin et al. |
| 3,839,516 A | 10/1974 | Williams et al. |
| 3,843,761 A | 10/1974 | Bierenbaum et al. |
| 3,872,014 A | 3/1975 | Schell |
| 3,933,647 A | 1/1976 | Müller |
| 3,956,112 A | 5/1976 | Lee et al. |
| 4,055,696 A | 10/1977 | Kamada et al. |
| 4,251,231 A | 2/1981 | Baird |
| 4,255,376 A | 3/1981 | Soehngen |
| 4,257,997 A | 3/1981 | Soehngen et al. |
| 4,276,179 A | 6/1981 | Soehngen |
| 4,298,693 A | 11/1981 | Wallace |
| 4,306,884 A | 12/1981 | Roth |
| 4,340,475 A | 7/1982 | Kraus et al. |
| 4,369,112 A | 1/1983 | Vincent et al. |
| 4,399,000 A | 8/1983 | Tedder |
| 4,405,688 A | 9/1983 | Lowery et al. |
| 4,441,891 A | 4/1984 | Roth |
| 4,510,242 A | 4/1985 | Tedder |
| 4,517,298 A | 5/1985 | Tedder |
| 4,520,213 A | 5/1985 | Victor |
| 4,532,347 A | 7/1985 | Vaughan |
| 4,581,236 A | 4/1986 | Bandel et al. |
| 4,617,127 A | 10/1986 | Light |
| 4,692,432 A | 9/1987 | Tedder |
| 4,717,482 A | 1/1988 | Light |
| 4,726,989 A | 2/1988 | Mrozinski |
| 4,778,688 A | 10/1988 | Matson |
| 4,789,468 A | 12/1988 | Sirkar |
| 4,865,973 A | 9/1989 | Kollerup et al. |
| 4,921,612 A | 5/1990 | Sirkar |
| 4,925,562 A | 5/1990 | te Hennepe et al. |
| 4,933,198 A | 6/1990 | Lee et al. |
| 4,966,707 A | 10/1990 | Cussler et al. |
| 4,973,434 A | 11/1990 | Sirkar et al. |
| 4,976,867 A | 12/1990 | Callahan et al. |
| 4,997,569 A | 3/1991 | Sirkar |
| 5,036,005 A | 7/1991 | Tedder |
| 5,084,220 A | 1/1992 | Møller |
| 5,096,584 A | 3/1992 | Reddy et al. |
| 5,120,594 A | 6/1992 | Mrozinski |
| 5,120,900 A | 6/1992 | Chen et al. |
| 5,215,902 A | 6/1993 | Tedder |
| 5,238,623 A | 8/1993 | Mrozinski |
| RE34,828 E | 1/1995 | Sirkar |
| 5,385,647 A | 1/1995 | Brueschke et al. |
| 5,449,457 A | 9/1995 | Prasad |
| 5,512,180 A | 4/1996 | Ho |
| 5,580,452 A | 12/1996 | Lin |

(Continued)

FOREIGN PATENT DOCUMENTS

CA 2003539 5/1991

(Continued)

OTHER PUBLICATIONS

C.L. Munson and C.J. King, "Factors Influencing Solvent Selection for Extraction of Ethanol from Aqueous Solutions", Ind. Eng. Chem. Process Des. Dev., 1984, 23, pp. 109-115.

(Continued)

*Primary Examiner*—Elvis O. Price (57) ABSTRACT

A method for obtaining ethanol from a feed solution utilizes an extractant comprising a mixture of at least one alkane and at least one aliphatic alcohol having the formula

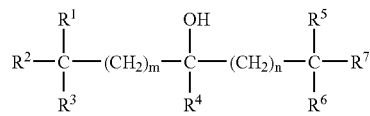

wherein $R^1$, $R^2$, $R^3$, $R^4$, $R^5$, and $R^7$ each independently represent H or a straight chain alkyl group having from 1 to 4 carbon atoms; $R^6$ represents a straight chain alkyl group having from 1 to 4 carbon atoms, or taken together $R^3$ and $R^6$ represent an alkylene group having from 1 to 4 carbon atoms; and m and n independently represent 0, 1, 2, or 3, with the proviso that if $R^4$ represents H, then at least two of $R^1$, $R^2$, and $R^3$, or at least one of $R^5$ and $R^7$, are straight chain alkyl groups having from 1 to 4 carbon atoms.

48 Claims, 3 Drawing Sheets

U.S. PATENT DOCUMENTS

| | | | |
|---|---|---|---|
| 5,620,605 | A | 4/1997 | Møller |
| 5,626,752 | A | 5/1997 | Mohn et al. |
| 5,632,946 | A | 5/1997 | Bacon, Jr. et al. |
| 5,711,882 | A | 1/1998 | Hofmann et al. |
| 5,714,072 | A | 2/1998 | Reed et al. |
| 5,961,832 | A | 10/1999 | Shaw et al. |
| 6,086,769 | A | 7/2000 | Kilambi et al. |
| 6,306,305 | B1 | 10/2001 | Harper |
| 6,656,362 | B1 | 12/2003 | Kihara et al. |

FOREIGN PATENT DOCUMENTS

| | | |
|---|---|---|
| EP | 324 922 A2 | 7/1989 |
| EP | 0 418 063 A1 | 3/1991 |
| EP | 480 567 A1 | 4/1992 |
| EP | 0 508 646 A1 | 10/1992 |
| EP | 246 065 B1 | 10/1992 |
| EP | 0 662 341 A1 | 7/1995 |
| EP | 0 771 585 A2 | 5/1997 |
| EP | 1 022 052 A2 | 7/2000 |
| GB | 155713 | 11/1979 |
| JP | 62-79808 | 4/1987 |
| JP | 63-80825 | 4/1988 |
| JP | 63-209704 | 8/1988 |
| JP | 06-210144 | 8/1994 |
| JP | 06-277463 | 10/1994 |
| JP | 06-327946 | 11/1994 |
| JP | 07-194933 | 8/1995 |
| JP | 07-313847 | 12/1995 |
| JP | 08-131783 | 5/1996 |
| JP | 08-155278 | 6/1996 |
| JP | 09-029076 | 2/1997 |
| JP | 09-057070 | 3/1997 |
| JP | 09-299947 | 11/1997 |
| JP | 11-207337 | 8/1999 |
| WO | WO 92/03216 | 3/1992 |
| WO | WO 93/23150 | 11/1993 |
| WO | WO 96/12541 | 5/1996 |
| WO | WO 01/09042 A1 | 2/2001 |

OTHER PUBLICATIONS

Ronald W. Rousseau, John Wiley & Sons, "Handbook of Separation Process Technology", A Wiley Interscience Publication, 1987, pp. 769-771..

R. Prasad and K.K. Sirkar, "Microporous Membrane Solvent Extraction", Separation Science and Technology, 1987, 22(2&3), pp. 619-640.

Von K. Wucherpfennig, K.D. Millies, M. Christmann, "Production of Wines With The Alcohol Removed Under Special Consideration of the Dialysis Method", Die Weinwirtschaft, Tech. 9-12, 1986, pp. 346-354. (With English Translation.).

Christopher Job, Cosima Schertler, Walter L. Staudenbauer, Eckhart Blass, "Selection of Organic Solvents for In Situ Extraction of Fermentation Products from Clostridium Thermohydrosulfuricum Cultures", Biotechnology Techniques, 3, 1989, 5, pp. 315-320.

A. Kiani, R.R. Bhave and K.K. Sirkar, "Solvent Extraction With Immobilized Interfaces in a Microporous Hydrophobic Membrane", Journal of Membrane Science, 20, 1984, pp. 125-145.

R. Prasad, A. Kiani, R.R. Bhave and K.K. Sirkar, "Further Studies on Solvent Extraction With Immobilized Interfaces in a Microporous Hydrophobic Membrane", Journal of Membrane Science, 1986, 26, pp. 79-97.

ASTM Test Method, "Standard Test Method for Pore Size Characteristics of Membrane Filters Using Automated Liquid Porosimeter", ASTM, E 1294—89 (Reapproved 1999), pp. 1-2.

Roddy, "Distribution of Ethanol-Water Mixtures to Organic Liquids", Ind. Eng. Chem. Process Des. Dev., vol. 20, No. 1, (1981) pp. 104-108.

METHOD FOR OBTAINING ETHANOL

FIELD

The present invention relates to methods for obtaining ethanol from a feed solution.

BACKGROUND

Commercial production of ethanol from fermentable feedstock (e.g., corn, biomass) is an important industrial process in which a mixture of fermentable feedstock in water is fermented by microorganisms, thereby producing a fermentation broth containing ethanol. Commercially produced ethanol is widely blended with gasoline (i.e., gasohol). For use in automobiles, gasohol should typically have sufficiently low water content such that, as blended with gasoline, water does not phase separate from the blend.

Ethanol may be obtained from a fermentation broth by a variety of techniques such as for example, pervaporation, distillation, or liquid-liquid extraction.

In pervaporation, ethanol in a fermentation broth is typically driven across a permselective membrane, emerging as vapor on the downstream side of the membrane, which is then condensed and collected. Reduced pressure at the downstream side of the membrane maintains the separation driving force. Pervaporation techniques are often relatively slow and frequently plagued by fouling of the permselective membrane by organic material that is typically ubiquitous in fermentation broths.

Distillation of a fermentation broth is typically energy intensive, and under most conditions, kills microorganisms in the fermentation broth and/or results in ethanol with undesirably high water content.

Liquid-liquid extraction is a method for transferring a solute dissolved in a first liquid to a second liquid that is essentially immiscible with the first liquid. The solution of the solute in the first liquid is generally termed a "feed solution", and the second liquid is generally termed an "extractant". As the feed solution is brought into contact with the extractant, the solute tends to distribute itself between the two liquids in accordance with the relative solubility of the solute in the two liquids. As practiced, liquid-liquid extraction methods are typically more energy efficient than distillation for obtaining ethanol from a feed solution. Further, ethanol obtained from a feed solution by liquid-liquid extraction methods may have a water content lower than that obtainable by distillation. The selection of an extractant typically depends on variables such as, for example, its affinity for ethanol and toxicity to microorganisms.

In a modification of the liquid-liquid extraction method, referred to hereinafter as "microporous membrane extraction", one side of a microporous membrane is typically contacted with the feed solution, and the opposing side of the microporous membrane with the extractant. A liquid-liquid interface, across which the solute is transferred, is thus formed between the feed solution and the extractant within micropores of the microporous membrane.

The overall efficiency of isolating a solute by liquid-liquid extraction methods depends on the efficiency with which the solute can be removed from the extractant and subsequently purified according to its intended use. Generally, the choice of extractant is highly influential to the overall process efficiency.

Because of the large scale of ethanol production, even minor improvements in overall efficiency of the extraction method may result in large economic savings that can make a significant difference (e.g., between profitability and economic unviability). Thus, there is a continuing need for more efficient methods for obtaining ethanol from a feed solution.

SUMMARY

In one aspect, the present invention provides a method for obtaining ethanol from a feed solution comprising:
  providing a feed solution comprising water and ethanol;
  providing an extractant that is immiscible with the feed solution, the extractant comprising a mixture of:
  at least one alkane; and
  at least one aliphatic alcohol having the formula wherein
  $R^1, R^2, R^3, R^4, R^5$, and $R^7$ each independently represent H or a straight chain alkyl group having from 1 to 4 carbon atoms,
  $R^6$ represents a straight chain alkyl group having from 1 to 4 carbon atoms, or taken together $R^3$ and $R^6$ represent an alkylene group having from 1 to 4 carbon atoms, and
  m and n independently represent 0, 1, 2, or 3,
  with the proviso that if $R^4$ represents H, then at least two of $R^1$, $R^2$,
  and $R^3$, or at least one of $R^5$ and $R^7$, are straight chain alkyl groups having from 1 to 4 carbon atoms;
  contacting the extractant with the feed solution; and
  at least partially removing ethanol from the extractant.

In another aspect, the present invention provides a method for obtaining ethanol from a feed solution comprising:
  providing a feed solution comprising water and ethanol;
  providing an extractant that is immiscible with the feed solution, the extractant comprising a mixture of:
  at least one alkane having a first yield factor for extraction of ethanol from the feed solution; and
  at least one branched aliphatic alcohol having from 6 to 12 carbon atoms, wherein the branched aliphatic alcohol has a second yield factor for extraction of ethanol from the feed solution,
  wherein the mixture has a third yield factor for extraction of ethanol from the feed solution, and further wherein the third yield factor is greater than both of the first and second yield factors;
  contacting the extractant with the feed solution; and
  at least partially removing ethanol from the extractant.

In some embodiments according to the present invention, a microporous membrane is utilized to facilitate extraction of ethanol from the feed solution.

In some embodiments, methods according to the present invention have high efficiencies for extraction of ethanol from a feed solution while simultaneously achieving low water content in the extractant.

DETAILED DESCRIPTION

The present invention concerns methods for obtaining ethanol from a feed solution.

Figure 1:
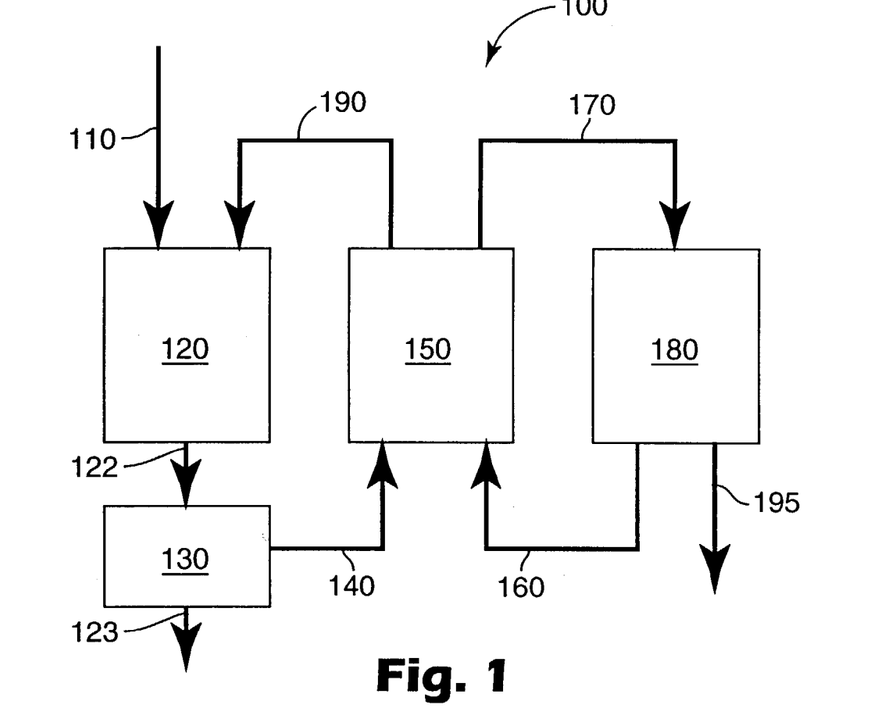
FIG. 1 is a schematic diagram of an exemplary process according to the present invention.

A flow diagram of one exemplary embodiment of the present invention is shown in FIG. 1. Accordingly, in method 100, feed stock 110 (i.e., water, microorganisms and fermentable material) is placed into fermenter 120 and allowed to form a fermentation broth 122. Insoluble material 123 in fermentation broth 122 is optionally removed (e.g., by sedimentation and/or filtration) in optional purifying unit 130 and resultant feed solution 140 is transported to extractor 150. In extractor 150, feed solution 140 and extractant 160 are brought into intimate contact with each other such that ethanol partitions between feed solution 140 and extractant 160. Extract 170, which contains extractant 160 and ethanol, is then transported to recovery unit 180 where ethanol 195, optionally mixed with water, is removed from extract 170 (e.g., by vacuum distillation) such that extractant 160 is regenerated and recycled into extractor 150. Likewise, extracted feed solution 190 is returned to fermenter 120, which is periodically replenished with additional feedstock 110 as necessary to replace components that have been removed during the process.

Feed solutions used in practice of the present invention comprise water and ethanol, and may be in the form of a solution, suspension, dispersion, or the like. In addition to ethanol and water, the feed solution may, optionally, contain soluble or insoluble components (e.g., fermentable sugars, saccharides, or polysaccharides, microorganisms, biomass). Examples of suitable biomass for the fermentation process include sugar-based materials (e.g., molasses, sugar cane, and sugar beets); and starch based materials (e.g., corn, wheat, cassava, barley, rye, and oats). Cellulosic biomass containing primarily cellulose, hemicellulose, and lignin plus varying amounts of other materials may be used as well. Similarly, the fermenting microorganism employed in connection with the present invention can be any known microorganism used in fermentation processes, including various species of alcohol producing fungi known as yeast, thermophilic bacteria, and various strains of Zymomonas bacteria. In some embodiments according to the present invention, the feed solution may comprise a fermentation broth and/or a filtrate (e.g., an ultrafiltrate) thereof.

Useful fermentation broths typically contain ethanol in an amount of from at least 0.5 percent by weight, 2 percent by weight, or 4 percent by weight up to at least 10 percent by weight based on the total weight of the fermentation broth, although higher and lower concentrations of ethanol may also be used.

Processes for preparing fermentation broths are well known. Typically, fermentation broths may be prepared by combining water, a fermentable sugar (or precursor thereof), and a microorganism such as, for example, brewer's yeast in a vessel (e.g., fermenter, vat), and maintaining the mixture at a temperature at which fermentation can occur (e.g., in a range of from about 15° C. to about 45° C.). Fermenters are widely commercially available and are described in, for example, U.S. Pat. No. 4,298,693 (Wallace).

The extractant comprises at least one alkane, and at least one branched $2^O$ or $3^O$ aliphatic alcohol. Useful branched 2 secondary or 3 tertiary aliphatic alcohols include those having the formula wherein $R^1$, $R^2$, $R^3$, $R^4$, $R^5$, and $R^7$ each independently represent H or a straight chain alkyl group having from 1 to 4 carbon atoms, $R^6$ represents a straight chain alkyl group having from 1 to 4 carbon atoms, or taken together $R^3$ and $R^6$ represent an alkylene group having from 1 to 4 carbon atoms, and m and n independently represent 0, 1, 2, or 3, with the proviso that if $R^4$ represents H, then at least two of $R^1$, $R^2$, and $R^3$, or at least one of $R^5$ and $R^7$, are straight chain alkyl groups having from 1 to 4 carbon atoms.

Typically, useful branched 2 secondary or 3 tertiary aliphatic alcohols are liquids under conditions utilized in practice of the present invention (e.g., at or above about 20° C.), although they may be solids as long as they form a homogenous liquid solution with the other components (e.g., the alkane) in the extractant. Aliphatic alcohols having from 6 to 12 carbons atoms typically have physical properties that make them suitable for use in practice of the present invention. Exemplary branched aliphatic alcohols include branched 2 secondary aliphatic alcohols (e.g., 2,6-dimethylcyclohexanol; 3,5-dimethylcyclohexanol; 4-methylcyclohexanol; 3,5-dimethylheptan-4-ol; 2,6-dimethylheptan-4-ol, and mixtures thereof) and branched 3 tertiary aliphatic alcohols (e.g., 3,6-dimethylheptan-3-ol, 2-methyl-2-nonanol, and mixtures thereof).

Useful alkanes may be linear (e.g., n-octane, n-nonane, n-decane, n-undecane, n-dodecane, n-tetradecane, n-hexadecane); branched (e.g., 2-methylnonane, 4-ethyl-2-methyloctane, 2,2-dimethyldecane, 4-methyldecane, 2,6-dimethyldecane); and/or cyclic (e.g., 1,2,4-trimethylcyclohexane, cis- and/or trans-decalin). Combinations of at least two alkanes (e.g., a combination of linear, branched, and/or cyclic alkanes) may be used.

The extractant may include components in addition to the alkane and branched 2 secondary or 3 tertiary aliphatic alcohol components. Such additional components may be intentionally added to the extractant or may be present, for example, as contaminants in the alkane or branched $2^O$ or $3^O$ aliphatic alcohol.

In order to ensure formation of a well-defined liquid-liquid interface, the extractant is typically selected to be immiscible with the feed solution. To reduce entrainment of the extractant in the feed solution, the extractant may be selected so that it is "substantially insoluble" in the feed solution (i.e., soluble to a degree of less than 2 percent by weight).

Depending on the choice of materials and conditions, gradual loss of extractant into the feed solution may occur during extraction. Unless recovered, extractant that becomes entrained or dissolved in the feed solution during extraction may adversely affect economic viability of the extraction process. Surprisingly, the extractant utilized in methods according to present invention typically reduces entrainment of the extractant in the feed solution.

Impurities and other components (e.g., alcohols and/or water) may be present in the extractant. If present, such impurities and other components may be present in an amount of less than about 20 percent by weight (e.g., less than 10 percent by weight, less than 5 percent by weight, or less than 2 percent by weight, based on the total weight of the extractant).

In order to facilitate separation of ethanol and/or water from the extractant by distillation (e.g., vacuum distillation), the extractant may be selected to have a boiling point higher than the boiling point of ethanol (i.e., 78.3° C.) and/or water although lower boiling extractants may be used. For example, the extractant may have a boiling point greater than 125° C. and/or greater than 150° C.

The feed solution and extractant may be utilized at any temperature at which they are liquids. Increasing the temperature of the feed solution and/or extractant typically results in a faster rate of extraction, however higher temperatures may adversely affect any microorganisms if a fermentation broth is used as a source for the feed solution. Thus, for continuous ethanol production using a fermentation broth containing brewer's yeast, at least one of the feed solution and extractant may be maintained at a temperature within a range of from about 26° C. to about 38° C., such as a temperature in a range of from 29° C. to 33° C. (e.g., 30.8° C.), although higher and lower temperatures may also be used. In some embodiments of the present invention, for example, methods wherein microorganisms are not employed or have been removed, the temperature may be successfully raised substantially, for example, to a temperature greater than about 50° C.

The extract comprises extractant and ethanol. In practice, the extract typically further comprises water, although the extract may contain no water. Ethanol, and optionally water, may be removed from the extract by any known means including, for example, pervaporation, evaporation (e.g., at reduced pressure), distillation (e.g., at elevated temperature and/or reduced pressure), and entrainment in a gas stream. Flash distillation (e.g., as described in U.S. Pat. No. 3,428,553 (Shiah)) is one particularly useful method for removing water and ethanol.

One measure of the efficiency of removal of ethanol from a specific feed solution with a specific extractant is the "yield factor". The yield factor for a specific selection of extractant and feed solution (expressed in units of grams (g) ethanol extracted per liter of feed solution extracted) is the product of the amount of ethanol extracted by the extractant from the feed solution per liter of feed solution during the extraction step multiplied by the purity of the extracted ethanol with respect to water, and is defined as follows:

$$\text{yield factor} = \left(\frac{\text{grams ethanol extracted}}{\text{liter of feed solution}}\right) \times \left(\frac{\text{grams ethanol}}{\text{grams ethanol} + \text{grams water}}\right)_{extract}$$

The quantity $$\left(\frac{\text{grams ethanol}}{\text{grams ethanol} + \text{grams water}}\right)_{extract}$$

reflects the composition that would be obtained if water and ethanol were separated from the extractant.

Typically, to promote rapid distribution of solute between the feed solution and the extractant, the feed solution and the extractant are intimately mixed. However, such intimate mixing may give rise to formation of stable emulsions (e.g., if the feed solution is a fermentation broth) that make separating feed solution from the extractant difficult. To reduce the problem of emulsion formation, a microporous membrane may be utilized during the extraction step.

Microporous membrane extraction techniques are well known, and representative such apparatuses have been described in, for example, U.S. Pat. No. RE 34,828 (Sirkar); U.S. Pat. No. 4,966,707 (Cussler et al.); and U.S. Pat. No. 3,956,112 (Lee et al.). Further, several useful microporous membrane extraction apparatuses are described in, for example, commonly-assigned U.S. patent application Ser. No. 10/388,099 entitled "LIQUID-LIQUID EXTRACTION SYSTEM AND METHOD", and filed concurrently herewith, the disclosure of which is incorporated herein by reference.

Figure 2:
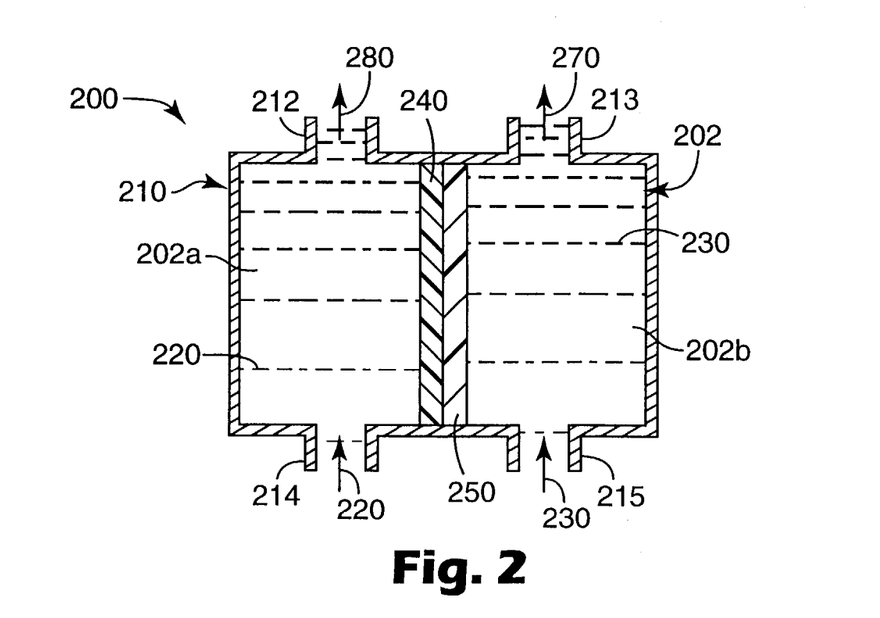
FIG. 2 is a cross-sectional schematic diagram of an exemplary microporous membrane extraction apparatus useful for practicing the process of the present invention.

An exemplary membrane extraction apparatus is depicted in FIG. 2, wherein membrane extraction apparatus 200 has fluid-tight housing 210 defining interior cavity 202, and having each of feed solution inlet port 214, extractant inlet port 215, extracted feed solution outlet port 212, and extract outlet port 213 extending therefrom. Microporous membrane 240 divides the interior cavity 202 into two chambers, denoted 202a and 202b, respectively. Optional porous support 250, if present, is located parallel and proximal to microporous membrane 240. As used in practice of the present invention, feed solution 220 enters chamber 202a through feed solution inlet port 214, and extractant 230 enters chamber 202b through extractant inlet port 215. Feed solution 220 penetrates microporous membrane 240 and forms a liquid-liquid interface (not shown) with extractant 230 within the micropores of the microporous membrane 240. Ethanol, and optionally water, diffuses from feed solution 220 into extractant 230, and resultant extract 270 leaves chamber 202b through extract outlet port 213. Likewise, the extracted feed solution 280 leaves chamber 202a through extracted feed solution outlet port 212.

The membrane extraction apparatus may be of any design as long as the extractant and feed solution have a liquid-liquid interface within at least one micropore, typically a plurality of micropores, of the microporous membrane. In general, the rate of ethanol extraction depends on the area of the liquid-liquid interface. Thus, membrane extraction apparatus designs that have large membrane surface areas are typically desirable, although designs having relatively smaller membrane surface areas may also be used.

To facilitate formation of an interface between the feed solution and the extractant within the microporous membrane, whichever of the feed solution or the extractant wets the membrane least well may be maintained at higher pressure than the other. For example, in the case of a hydrophobic microporous membrane the feed solution may have a higher fluid pressure than the extractant. This pressure differential should typically be sufficient to substantially immobilize the interface between the feed solution and extractant, but preferably not large enough to cause damage to the microporous membrane. The pressure differential may be achieved by a variety of known means including a restriction valve (e.g., a back-pressure valve on either of outlet ports 212 or 213), a fluid height differential, or the like. If present, the pressure differential between the feed solution and the extractant may be, for example, at least 10 cm water at 4° C. (1 kPa), at least 1 PSI (6.9 kPa), and may be up to about 13 PSI (90 kPa), although higher and lower pressures may also be used.

Microporous membranes used in practice of the present invention typically have micrometer-sized pores (i.e., micropores) that extend between major surfaces of the membrane. The micropores may be, for example, isolated or interconnected. The microporous membrane may be formed from any material having micropores therethrough, for example, a microporous thermoplastic polymer. The microporous membrane may, for example, be flexible or rigid. In some embodiments according to the present invention, useful thermoplastic microporous membranes may comprise a blend of similar or dissimilar thermoplastic polymers, each optionally having a different molecular weight distribution (e.g., a blend of ultrahigh molecular weight polyethylene (UHMWPE) and high molecular weight polyethylene (HMWPE)).

Micropore size, thickness, and composition of the microporous membranes typically determine the rate of ethanol extraction according to the present invention. The size of the micropores of the microporous membrane should be sufficiently large to permit contact between the feed solution and the extractant within the micropores, but not so large that flooding of the feed solution through the microporous membrane into the extractant occurs.

Microporous membranes useful for practice of the present invention may be, for example, hydrophilic or hydrophobic. Microporous membranes can be prepared by methods well known in the art and described in, for example, U.S. Pat. No. 3,801,404 (Druin et al.); U.S. Pat. No. 3,839,516 (Williams et al.); U.S. Pat. No. 3,843,761 (Bierenbaum et al.); U.S. Pat. No. 4,255,376 (Soehngen et al.); U.S. Pat. No. 4,257,997 (Soehngen et al.); U.S. Pat. No. 4,276,179 (Soehngen); U.S. Pat. No. 4,973,434 (Sirkar et al.), and/or are widely commercially available from suppliers such as, for example, Celgard, Inc. (Charlotte, N.C.); Tetratec, Inc. (Ivyland, Pa.); Nadir Filtration GmbH (Wiesbaden, Germany); or Membrana, GmbH (Wuppertal, Germany). Exemplary hydrophilic membranes include membranes of microporous polyamide (e.g., microporous nylon), microporous polycarbonate, microporous ethylene vinyl alcohol copolymer, and microporous hydrophilic polypropylene. Exemplary hydrophobic membranes include membranes of microporous polyethylene, microporous polypropylene (e.g., thermally induced phase separation microporous polypropylene), and microporous polytetrafluoroethylene.

Typically, the mean pore size of useful microporous membranes (e.g., as measured according to ASTM E 1294-89 (1999) "Standard Test Method for Pore Size Characteristics of Membrane Filters Using Automated Liquid Porosimeter") may be greater than about 0.07 micrometer (e.g., greater than about 0.1 micrometer or greater than about 0.25 micrometer), and may be less than about 1.4 micrometers (e.g., less than about 0.4 micrometer or less than about 0.3 micrometer), although microporous membranes having larger or smaller mean pore sizes may also be used. In order to reduce emulsion formation and/or flooding across the membrane, the microporous membrane may be substantially free of pores, tears, or other holes that exceed about 100 micrometers in diameter.

Useful microporous membranes typically have a porosity in a range of from at least about 20 percent (e.g., at least about 30 percent or at least about 40 percent) up to about 80 percent, about 87 percent, or even about 95 percent, based on the volume of the microporous membrane.

Typically, useful microporous membranes have a thickness of at least about 25 micrometers (e.g., at least about 35 micrometers or at least about 40 micrometers), and/or may have a thickness of less than about 80 micrometers (e.g., less than about 60 micrometers or even less than about 50 micrometers), although membranes of any thickness may be used. Typically, microporous membranes should be mechanically strong enough, alone or in combination with an optional porous support member, to withstand any pressure difference that may be imposed across the microporous membrane under the intended operating conditions.

According to the present invention, multiple microporous membranes may be used in series or in parallel. Exemplary membrane forms include sheets, bags, and tubes, that may be substantially planar, or nonplanar (e.g., pleated, spiral wound cartridge, plate-frame, hollow fiber bundle). In some embodiments according to the present invention, a microporous membrane may comprise a microporous hollow fiber membrane as described in, for example, U.S. Pat. No. 4,055,696 (Kamada et al.); U.S. Pat. No. 4,405,688 (Lowery et al.); U.S. Pat. No. 5,449,457 (Prasad), the disclosures of which are incorporated herein by reference. Of course, the nature of the extraction apparatus (e.g., shape, size, components) may vary depending on the form of the membrane chosen.

The microporous membrane may comprise at least one hydrophobic (i.e., not spontaneously wet out by water) material. Exemplary hydrophobic materials include polyolefins (e.g., polypropylene, polyethylene, polybutylene, copolymers of any of the forgoing and, optionally, an ethylenically unsaturated monomer), and combinations thereof. If the microporous membrane is hydrophobic, a positive pressure may be applied to the feed solution relative to the extractant to aid in wetting the microporous membrane.

In some embodiments according to the present invention, the microporous membrane may be hydrophilic, for example, a hydrophilic microporous polypropylene membrane having a nominal average pore size in a range of from 0.2 to 0.45 micrometers (e.g., as marketed under the trade designation "GH POLYPRO MEMBRANE" by Pall Life Sciences, Inc., Ann Arbor, Mich.). If the microporous membrane is hydrophilic, positive pressure may be applied to the extractant relative to the feed solution to facilitate immobilization of the liquid-liquid interface within the membrane. Exemplary membranes include microporous membranes as described in U.S. Pat. No. 3,801,404 (Druin et al.); U.S. Pat. No. 3,839,516 (Williams et al.); U.S. Pat. No. 3,843,761 (Bierenbaum et al.); U.S. Pat. No. 4,255,376 (Soehngen); U.S. Pat. No. 4,257,997 (Soehngen et al.); and U.S. Pat. No. 4,276,179 (Soehngen); U.S. Pat. No. 4,726,989 (Mrozinski); U.S. Pat. No. 5,120,594 (Mrozinski); and U.S. Pat. No. 5,238,623 (Mrozinski), the disclosures of which are incorporated herein by reference.

If desired, ethanol obtained according to the present invention may be further purified using known techniques (e.g., molecular sieves, azeotropic distillation with benzene).

The present invention will be more fully understood with reference to the following non-limiting examples in which all parts, percentages, ratios, and so forth, are by weight unless otherwise indicated.

EXAMPLES

Unless otherwise noted, all reagents used in the examples were obtained, or are available, from general chemical suppliers such as Aldrich Chemical Company, Milwaukee, Wis., or may be synthesized by known methods.

Examples 1–39 and Comparative Examples A–N

Examples 1–39 and Comparative Examples A–N were carried out according to the following procedure:

Two g of a 9.3 percent by weight solution of ethanol in water was placed in a 1.5 dram (6 mL) vial at 23° C. with 1 g of extractant to be tested. The vial was sealed and vigorously shaken by hand for 3 minutes, allowed to stand for five minutes, and again vigorously shaken for three minutes. The vial was then allowed to stand for 48 hours to allow the liquid phases to separate. Aliquots of both the aqueous and organic phases were analyzed for ethanol and water by gas chromatography using a MODEL 6890 gas chromatograph obtained from Hewlett-Packard Company (Palo Alto, Calif.) equipped with a thermal conductivity detector and a 98 foot (30 m), 530 micrometer inner diameter capillary column having a polyether liquid phase (having the trade designation "CARBOWAX"). Helium was used as the carrier gas. The chromatograph oven temperature was initially set at 40° C. and was increased to 230° C. at a rate of 20° C./minute after each aliquot was injected onto the column. Integrated peak areas for ethanol and water were determined and corrected to account for differences in their respective detector response factors. Yield factors were calculated as described hereinabove and are reported in Table 1 (below).

TABLE 1

|  | ALIPHATIC ALCOHOL | PARTS OF ALCOHOL | ALKANE | PARTS OF ALKANE | YIELD FACTOR |
| --- | --- | --- | --- | --- | --- |
| COMPARATIVE EXAMPLE A | — | — | decalin | 100 | 0 |
| COMPARATIVE EXAMPLE B | — | — | dodecane | 100 | 111 |
| COMPARATIVE EXAMPLE C | — | — | tetradecane | 100 | 52 |
| COMPARATIVE EXAMPLE D | oleyl alcohol | 100 | — | — | 273 |
| COMPARATIVE EXAMPLE E | 4-methylcyclohexanol | 100 | — | — | 334 |
| 1 | 4-methylcyclohexanol | 78 | dodecane | 22 | 479 |
| 2 | 4-methylcyclohexanol | 54 | dodecane | 46 | 519 |
| 3 | 4-methylcyclohexanol | 43 | dodecane | 57 | 160 |
| COMPARATIVE EXAMPLE F | 2,6-dimethylcyclohexanol | 100 | — | — | 219 |
| 4 | 2,6-dimethylcyclohexanol | 74 | dodecane | 26 | 684 |
| 5 | 2,6-dimethylcyclohexanol | 52 | dodecane | 48 | 364 |
| COMPARATIVE EXAMPLE G | 3,5-dimethylcyclohexanol | 100 | — | — | 561 |
| 6 | 3,5-dimethylcyclohexanol | 69 | dodecane | 31 | 738 |
| 7 | 3,5-dimethylcyclohexanol | 33 | dodecane | 67 | 708 |
| COMPARATIVE EXAMPLE H | 2,6-dimethyl-4-heptanol | 100 | — | — | 866 |
| 8 | 2,6-dimethyl-4-heptanol | 88 | dodecane | 12 | 1466 |
| 9 | 2,6-dimethyl-4-heptanol | 80 | dodecane | 20 | 1618 |
| 10 | 2,6-dimethyl-4-heptanol | 73 | dodecane | 27 | 2012 |
| 11 | 2,6-dimethyl-4-heptanol | 63 | dodecane | 37 | 2232 |
| 12 | 2,6-dimethyl-4-heptanol | 59 | dodecane | 41 | 1503 |
| 13 | 2,6-dimethyl-4-heptanol | 43 | dodecane | 57 | 484 |
| 14 | 2,6-dimethyl-4-heptanol | 27 | dodecane | 73 | 392 |
| 15 | 2,6-dimethyl-4-heptanol | 14 | dodecane | 86 | 51 |
| 16 | 2,6-dimethyl-4-heptanol | 69 | decalin | 31 | 1129 |
| 17 | 2,6-dimethyl-4-heptanol | 35 | decalin | 65 | 1199 |
| COMPARATIVE EXAMPLE I | 3,6-dimethyl-3-heptanol | 100 | — | — | 1536 |
| 18 | 3,6-dimethyl-3-heptanol | 88.5 | tetradecane | 11.5 | 1587 |
| 19 | 3,6-dimethyl-3-heptanol | 78 | tetradecane | 22 | 1621 |
| 20 | 3,6-dimethyl-3-heptanol | 65 | tetradecane | 35 | 1607 |
| 21 | 3,6-dimethyl-3-heptanol | 48 | tetradecane | 52 | 111 |
| 22 | 3,6-dimethyl-3-heptanol | 37 | tetradecane | 63 | 204 |
| 23 | 3,6-dimethyl-3-heptanol | 18 | tetradecane | 82 | 182 |
| COMPARATIVE EXAMPLE J | 3-methyl-3-octanol | 100 | — | — | 410 |
| 24 | 3-methyl-3-octanol | 89 | dodecane | 11 | 398 |
| 25 | 3-methyl-3-octanol | 68 | dodecane | 32 | 542 |
| 26 | 3-methyl-3-octanol | 45 | dodecane | 55 | 242 |
| COMPARATIVE EXAMPLE K | 3,7-dimethyl-3-octanol | 100 | — | — | 675 |
| 27 | 3,7-dimethyl-3-octanol | 85 | dodecane | 15 | 709 |
| 28 | 3,7-dimethyl-3-octanol | 55 | dodecane | 45 | 170 |
| 29 | 3,7-dimethyl-3-octanol | 38 | dodecane | 62 | 508 |
| COMPARATIVE EXAMPLE L | 2-methyl-2-nonanol | 100 | — | — | 520 |
| 30 | 2-methyl-2-nonanol | 83 | dodecane | 17 | 611 |
| 31 | 2-methyl-2-nonanol | 51 | dodecane | 49 | 565 |
| 32 | 2-methyl-2-nonanol | 33 | dodecane | 67 | 329 |

TABLE 1-continued

|  | ALIPHATIC ALCOHOL | PARTS OF ALCOHOL | ALKANE | PARTS OF ALKANE | YIELD FACTOR |
|---|---|---|---|---|---|
| COMPARATIVE EXAMPLE M | 6-ethyl-3-decanol | 100 | — | — | 243 |
| 33 | 6-ethyl-3-decanol | 77 | dodecane | 23 | 513 |
| 34 | 6-ethyl-3-decanol | 56 | dodecane | 44 | 488 |
| 35 | 6-ethyl-3-decanol | 43 | dodecane | 57 | 162 |
| COMPARATIVE EXAMPLE N | 7-ethyl-2-methyl-4-undecanol | 100 | — | — | 565 |
| 36 | 7-ethyl-2-methyl-4-undecanol | 84 | dodecane | 16 | 596 |
| 37 | 7-ethyl-2-methyl-4-undecanol | 73 | dodecane | 27 | 966 |
| 38 | 7-ethyl-2-methyl-4-undecanol | 53 | dodecane | 47 | 1070 |
| 39 | 7-ethyl-2-methyl-4-undecanol | 40 | dodecane | 60 | 166 |

Figure 3:
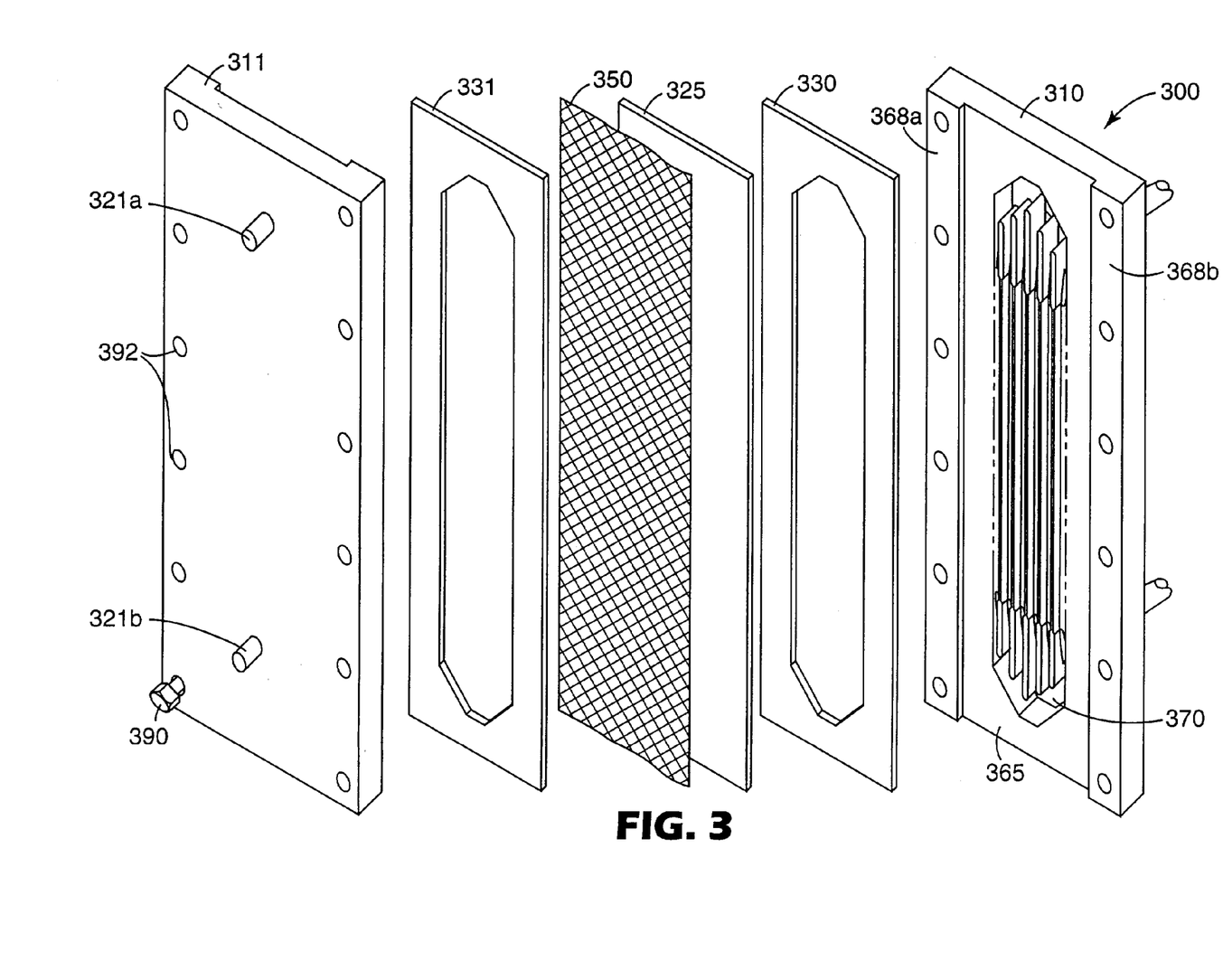
FIG. 3 is an exploded view of a membrane extraction apparatus used in Example 40 and Comparative Example O.
Figure 4:
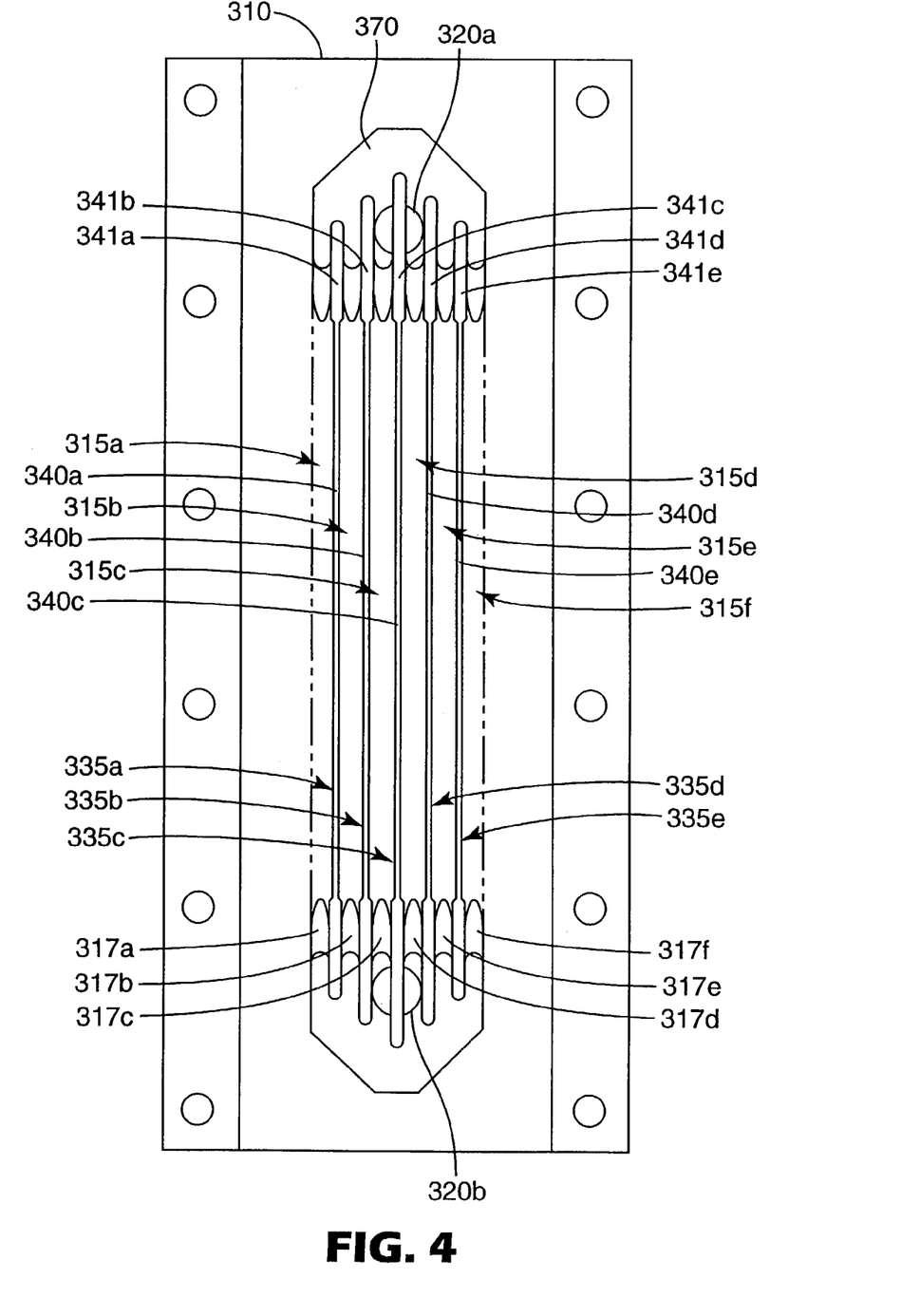
FIG. 4 is a top view of an aluminum plate used in the membrane extraction apparatus of FIG. 3.

A membrane extraction apparatus of the type shown in FIGS. 3 and 4 was used in Example 40 and Comparative Example O.

The membrane extraction apparatus 300 consisted of two identical 1.27 cm thick aluminum frames 310, 311 (i.e., feed frame 310 and extractant frame 311, respectively). For simplicity, the following discussion of dimensions will refer only to aluminum feed frame 310. Front face 365 was 0.08 cm lower relative to raised edge portions 368a, 368b of feed frame 310. Feed frame 310 had an elongated hexagonal membrane contact region 370 that was 38.8 cm in length. Channels 315a,b,c,d,e,f were separated by ribs 335a,b,c,d,e, each rib having a respective central portion 340a,b,c,d,e and opposed end sections 341a,b,c,d,e. Ports 320a,b were cut through frame 310 at both ends of the flow channels. Channels 315a,b,c,d,e,f measured 26.4 cm between descending tapers 317a,b,c,d,e,f located at both ends of each respective channel. The bottom surface of each channel (between descending tapers) was coplanar with recessed region 365. Channels 315b,c,d,e were 0.9 cm wide. In use, the width of each of channels 315a,f was 0.6 cm, with the outer edge of the channel being determined by a central opening (not shown) in gasket 330, corresponding in size and shape to elongated hexagonal membrane contact region 370. Channels 315a,b,c,d,e,f each terminated in a gradual taper that descended 0.5 cm over a 2.5 cm distance. The tops of ribs 335a,b,c,d,e were co-planar with raised shoulders 368a, 368b (i.e., they were 0.08 cm higher than the bottom surfaces of channels 315a,b,c,d,e,f). Central portions 340a, b,c,d,e of ribs 335a,b,c,d,e were 0.08 cm wide. End sections 341a,b,c,d,e were each 0.3 cm wide and had a maximum depth of 1.4 cm relative to raised shoulders 368a, 368b. End sections 341a,e were 3.5 cm in length; end sections 341b,d were 4.5 cm in length; and end sections 341c were 5.2 cm in length.

Polyethylene mesh 350 having 0.3 cm by 0.3 cm square openings was placed between channels 315a,b,c,d,e,f and microporous membrane 325 on the lower pressure (solvent) side of membrane extraction apparatus 300. Microporous membrane 325 was sealed between polychloroprene gaskets 330, 331 and frames 310, 311 using bolts 390 inserted through holes 392 extending through frames 310, 311. Polychloroprene gaskets 330, 331 were 0.16 cm thick, and each had a central opening corresponding to elongated hexagonal membrane contact region 370.

Microporous membrane 325 was a hydrophobic microporous polypropylene membrane, made by the thermally induced phase separation process according to the method of U.S. Pat. No. 5,120,594 (Mrozinski), and had a thickness of 38 micrometers and an average pore size of 0.20–0.21 micrometers (largest pore size was 0.32 micrometers). The extractant/membrane/fermentation broth contact area was 187 cm$^2$. After assembly, membrane extraction apparatus 300 was positioned such that its long axis was vertically oriented. Fermentation broth (982 g) with a 10 percent by weight ethanol content (obtained from Minnesota Corn Processors, LLC, Marshall, Minn.) was circulated continuously through ports 320a,b using a gear pump. Extractant (219 g) was continuously circulated (parallel to the feed solution flow direction) through ports 321a,b using a gear pump equipped with fluoroelastomer seals. The liquids were circulated from beakers to the lower ports of the cell; fluid pressures were maintained by backpressure valves (not shown) attached to ports 320a and 321a and were measured with pressure gages.

Example 40

The fermentation broth, extractant, and the membrane extraction apparatus were each maintained at 35° C. Fermentation broth (982 g, 10 percent by weight ethanol content obtained from Minnesota Corn Processors, LLC, Marshall, Minn.) was circulated through the extraction apparatus at a rate of 2 mL/second and a pressure of 3.2 psi (22 kPa); the extractant (219 g, blend of 63 percent by weight 2,6-dimethyl-4-heptanol and 37 percent by weight dodecane) was circulated through the extraction apparatus at a rate of 4 mL/second and maintained at a pressure of 1.3 psi (8.9 kPa). Extractions were run for 3 hours, with 1 mL aliquots of the extract and broth taken at intervals. Aliquots were analyzed by gas chromatography (as in Example 1) for ethanol and water in the extractant, and for solvent contamination in the broth. Throughout each extraction, the extractant remained clear, and no emulsion formation was observed. The content of ethanol and water (in percent by weight of the total) in the extractant was measured over time, and is reported in Table 2 (below)

TABLE 2

| Time, hours | Ethanol, wt. % | H$_2$O, wt. % | Ethanol Transfer, g | Ethanol/H$_2$O, wt./wt. |
|---|---|---|---|---|
| 0 | 0 | 0 | 0 | — |
| 0.03 | 0.10 | 0.49 | 0.23 | 0.21 |
| 0.17 | 0.30 | 0.46 | 0.66 | 0.91 |
| 0.33 | 0.42 | 0.43 | 0.91 | 0.96 |
| 0.67 | 0.80 | 0.56 | 1.75 | 1.44 |
| 1.00 | 1.08 | 0.60 | 2.37 | 1.80 |
| 1.50 | 1.53 | 0.75 | 3.35 | 2.05 |
| 2.00 | 1.62 | 0.82 | 3.54 | 1.97 |

TABLE 2-continued

| Time, hours | Ethanol, wt. % | H$_2$O, wt. % | Ethanol Transfer, g | Ethanol/H$_2$O, wt./wt. |
|---|---|---|---|---|
| 2.50 | 1.85 | 0.81 | 4.04 | 2.27 |
| 3.00 | 2.13 | 0.89 | 4.67 | 2.40 |

The concentration of 2,6-dimethyl-4-heptanol in the fermentation broth as a function of time is reported in Table 3 (below).

TABLE 3

| Time, hours | 2,6-Dimethyl-4-heptanol in Fermentation Broth, wt. % |
|---|---|
| 0.0167 | 0.000 |
| 0.5 | 0.016 |
| 1 | 0.029 |
| 2 | 0.045 |
| 3 | 0.048 |

Comparative Example O

Example 40 was repeated, except that the extractant was undiluted 2,6-dimethyl-4-heptanol, and the fermentation broth was circulated through the extraction apparatus at a rate of 3 mL/second and a pressure of 3 psi (21 kPa), while the extractant was circulated through the extraction apparatus at a rate of 6 mL/second and maintained at a pressure of 1.5 psi (10 kPa). The content of ethanol and water (in percent by weight of the total) in the extractant was measured over time, and is reported in Table 4 (below).

TABLE 4

| Time, hours | Ethanol, wt. % | H$_2$O, wt. % | Ethanol Transfer, g | Ethanol/H$_2$O, wt./wt. |
|---|---|---|---|---|
| 0 | 0 | 0 | 0 | — |
| 0.03 | 0.11 | 1.61 | 0.24 | 0.69 |
| 0.17 | 0.32 | 0.73 | 0.71 | 0.44 |
| 0.33 | 0.57 | 0.86 | 1.25 | 0.66 |
| 0.67 | 1.02 | 1.03 | 2.23 | 0.99 |
| 1.00 | 1.44 | 1.21 | 3.15 | 1.19 |
| 1.50 | 2.56 | 1.89 | 5.60 | 1.35 |
| 2.00 | 3.14 | 2.81 | 6.87 | 1.12 |
| 2.50 | 2.40 | 1.52 | 5.26 | 1.58 |
| 3.00 | 3.67 | 2.22 | 8.05 | 1.65 |

The concentration of 2,6-dimethyl-4-heptanol in the fermentation broth as a function of time is reported in Table 5 (below).

TABLE 5

| Time, hours | 2,6-Dimethyl-4-heptanol in Fermentation Broth, wt. % |
|---|---|
| 0.0167 | 0.013 |
| 0.5 | 0.030 |
| 1 | 0.038 |
| 2 | 0.089 |
| 3 | 0.154 |

Various modifications and alterations of this invention will become apparent to those skilled in the art without departing from the scope and spirit of this invention, and it should be understood that this invention is not to be unduly limited to the illustrated embodiments set forth herein.

What is claimed is:

1. A method for obtaining ethanol from a feed solution comprising:
providing a feed solution comprising water and ethanol;
providing an extractant that is immiscible with the feed solution, the extractant comprising a mixture of:
at least one alkane; and
at least one aliphatic alcohol having the formula wherein
R$^1$, R$^2$, R$^3$, R$^4$, R$^5$, and R$^7$ each independently represent H or a straight chain alkyl group having from 1 to 4 carbon atoms,
R$^6$ represents a straight chain alkyl group having from 1 to 4 carbon atoms, or taken together R$^3$ and R$^6$ represent an alkylene group having from 1 to 4 carbon atoms, and
m and n independently represent 0, 1, 2, or 3,
with the proviso that if R$^4$ represents H, then at least two of R$^1$, R$^2$, and R$^3$, or at least one of R$^5$ and R$^7$, are straight chain alkyl groups having from 1 to 4 carbon atoms;
contacting the extractant with the feed solution; and
at least partially removing ethanol from the extractant.

2. A method according to claim 1, wherein removing comprises evaporating.

3. A method according to claim 1, wherein removing comprises distilling.

4. A method according to claim 1, wherein removing comprises pervaporation.

5. A method according to claim 1, wherein the extractant has a boiling point of at least 125° C.

6. A method according to claim 1, wherein the extractant has a boiling point of at least 150° C.

7. A method according to claim 1, wherein the feed solution comprises a fermentation broth.

8. A method according to claim 1, wherein the aliphatic alcohol is selected from 3,6-dimethylheptan-3-ol, 2,6-dimethylheptan-4-ol, or a combination thereof.

9. A method according to claim 1, wherein the feed solution comprises ethanol in a concentration of at least 2 percent by weight.

10. A method according to claim 1, wherein the temperature of the feed solution is greater than about 29° C.

11. A method according to claim 1, wherein the temperature of the feed solution is in a range of from about 29° C. to about 33° C.

12. A method according to claim 1, wherein the process is carried out in a continuous manner.

13. A method according to claim 3, wherein the process is carried out in a continuous manner.

14. A method according to claim 1, wherein the at least one alkane comprises decane, dodecane, tetradecane, or a mixture thereof.

15. A method according to claim 1, further comprising:
providing a membrane having a plurality of micropores; and contacting the membrane with the extractant and the feed solution, wherein the extractant and the feed solution contact each other within at least one micropore of the membrane.

16. A method according to claim 15, wherein the microporous membrane has an average pore size in a range of from about 0.1 micrometer to about 0.4 micrometer.

17. A method according to claim 15, wherein the microporous membrane is hydrophilic.

18. A method according to claim 15, wherein the microporous membrane is hydrophobic.

19. A method according to claim 15, wherein the microporous membrane comprises a thermoplastic polymer.

20. A method according to claim 15, wherein the microporous membrane comprises a blend of thermoplastic polymers.

21. A method according to claim 15, wherein the microporous membrane comprises polyolefin.

22. A method according to claim 15, wherein the microporous membrane comprises polypropylene.

23. A method according to claim 15, wherein removing comprises evaporating.

24. A method according to claim 15, wherein removing comprises distilling.

25. A method according to claim 24, wherein the process is carried out in a continuous manner.

26. A method according to claim 15, wherein removing comprises pervaporation.

27. A method according to claim 15, wherein the extractant has a boiling point of at least 125° C.

28. A method according to claim 15, wherein the extractant has a boiling point of at least 150° C.

29. A method according to claim 15, wherein the feed solution comprises fermentation broth.

30. A method according to claim 15, wherein the aliphatic alcohol is selected from 3,6-dimethylheptan-3-ol, 2,6-dimethylheptan-4-ol, and a combination thereof.

31. A method according to claim 15, wherein the alkane is selected from decane, dodecane, and a combination thereof.

32. A method according to claim 15, wherein the process is carried out in a continuous manner.

33. A method according to claim 15, wherein the pressure of the feed solution is at least 1 kPa greater than the pressure of the extractant.

34. A method according to claim 15, wherein the pressure of the feed solution is at least 6.9 kPa greater than the pressure of the extractant.

35. A method for obtaining ethanol from a feed solution comprising:

providing a feed solution comprising water and ethanol;
providing an extractant that is immiscible with the feed solution, the extractant comprising a mixture of:
at least one alkane having a first yield factor for extraction of ethanol from the feed solution; and
at least one branched aliphatic alcohol having from 6 to 12 carbon atoms, wherein the branched aliphatic alcohol has a second yield factor for extraction of ethanol from the feed solution,
wherein the mixture has a third yield factor for extraction of ethanol from the feed solution, and further wherein the third yield factor is greater than both of the first and second yield factors;
contacting the extractant with the feed solution; and
at least partially removing ethanol from the extractant.

36. A method according to claim 35, wherein removing comprises evaporating.

37. A method according to claim 35, wherein removing comprises distilling.

38. A method according to claim 35, wherein removing comprises pervaporation.

39. A method according to claim 35, further comprising:
providing a membrane having a plurality of micropores; and
contacting the membrane with the extractant and the feed solution, wherein the extractant and the feed solution contact each other within at least one micropore of the membrane.

40. A method according to claim 39, wherein the microporous membrane is hydrophilic.

41. A method according to claim 39, wherein the microporous membrane is hydrophobic.

42. A method according to claim 39, wherein the microporous membrane has an average pore size in a range of from about 0.1 micrometer to about 0.4 micrometer.

43. A method according to claim 39, wherein the microporous membrane comprises a thermoplastic polymer.

44. A method according to claim 39, wherein the microporous membrane comprises a blend of thermoplastic polymers.

45. A method according to claim 39, wherein the feed solution comprises fermentation broth.

46. A method according to claim 39, wherein the pressure of the feed solution is at least 1 kPa greater than the pressure of the extractant.

47. A method according to claim 39, wherein the pressure of the feed solution is at least 6.9 kPa greater than the pressure of the extractant.

48. A method according to claim 39, wherein the process is carried out in a continuous manner.

* * * * *